(12) United States Patent
Park et al.

(10) Patent No.: US 7,485,265 B2
(45) Date of Patent: Feb. 3, 2009

(54) CERAMIC ELECTRODE STRUCTURE FOR GENERATING IONS, AND ION GENERATING APPARATUS USING THE SAME

(75) Inventors: Rae Eun Park, Suwon (KR); Eun Ju Ha, Ulsan (KR); Jun-Hyoun Kwon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 841 days.

(21) Appl. No.: 11/102,816

(22) Filed: Apr. 11, 2005

(65) Prior Publication Data

US 2006/0024219 A1 Feb. 2, 2006

(30) Foreign Application Priority Data

Jul. 27, 2004 (KR) .................. 10-2004-0058859

(51) Int. Cl.
*B01J 19/08* (2006.01)
(52) U.S. Cl. ................... 422/186.04; 361/231

(58) Field of Classification Search ........... 422/186.04; 361/231
See application file for complete search history.

(56) References Cited

U.S. PATENT DOCUMENTS 7,256,979 B2 * 8/2007 Sekoguchi et al. .......... 361/231

FOREIGN PATENT DOCUMENTS

| JP | 05-242956 A | 9/1993 |
|----|-------------|--------|
| JP | 2003-36954 A | 2/2003 |
| JP | 2003-47651 A | 2/2003 |
| JP | 2003-161494 A | 6/2003 |
| JP | 2003-187945 A | 7/2003 |

* cited by examiner

*Primary Examiner*—Kishor Mayekar
(74) *Attorney, Agent, or Firm*—Sughrue Mion, PLLC

(57) ABSTRACT

A ceramic electrode structure designed to have an enhanced construction, wherein an induction electrode has an area larger than that of a discharge electrode. A high square pulse voltage is applied to the enhanced ceramic electrode structure, thereby increasing an efficiency of ion generation and effectively restricting generation of ozone.

12 Claims, 13 Drawing Sheets

FIG. 4

| | | D1 | D2 | D3 | D4 | D5 |
|---|---|---|---|---|---|---|
| Ceramic electrode data | Electrode capacitance (pF) | 11 | 7 | 5 | 20 | 31 |
| | Area of discharge electrode (mm$^2$) | 51.27 | 33.85 | 33.85 | 66.52 | 76.68 |
| | Area of induction electrode (mm$^2$) | 55.04 | 55.04 | 28.75 | 146.20 | 239.83 |
| | Area ratio of induction electrode to discharge electrode | 1.07 | 1.63 | 0.85 | 2.2 | 3.13 |
| | Area ratio of total area to discharge electrode | 9.2 | 6.1 | 6.1 | 12.0 | 13.8 |
| Result of experiment | Starting voltage [kV] | 2.9 | 3.0 | 2.9 | 2.4 | 2.6 |
| | High Voltage [kV] | 4.0 | 3.9 | 4.2 | 3.3 | 3.0 |
| | Amount of ions (×10$^4$) | 7 | 21 | 4 | 83 | 103 |

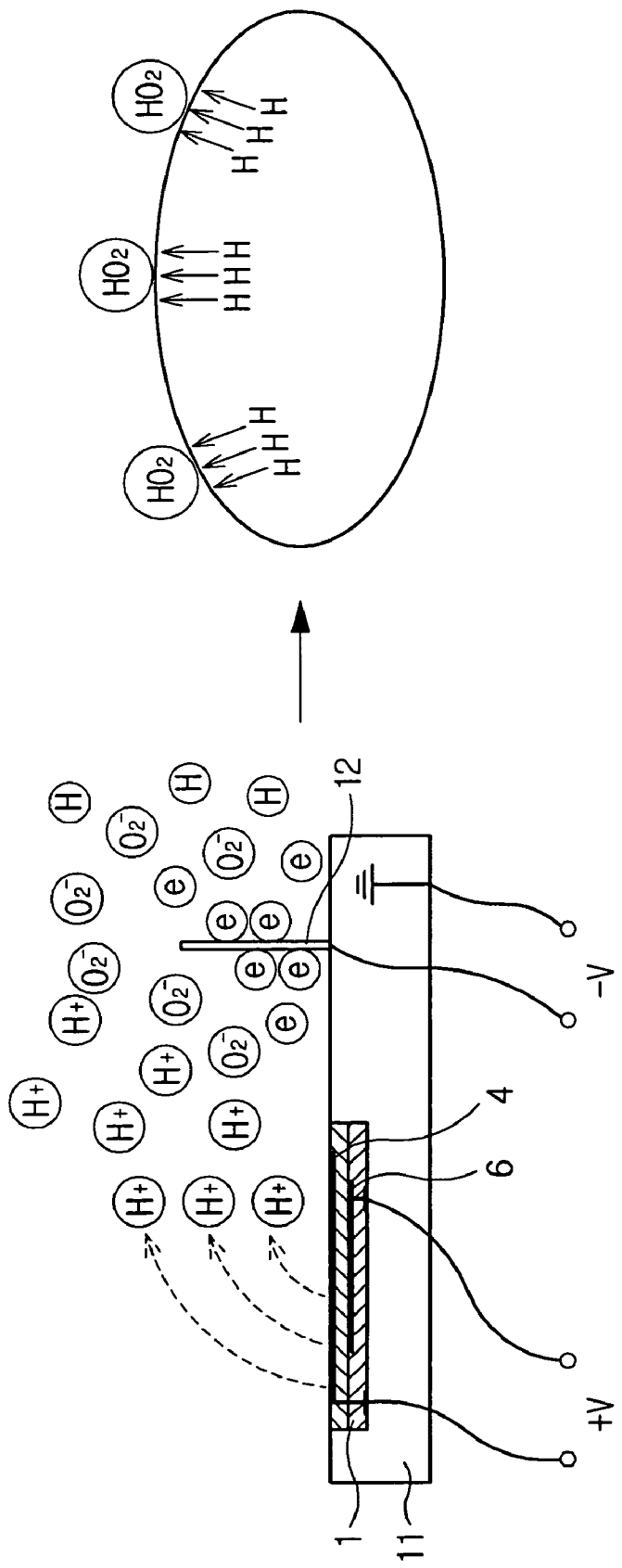

CERAMIC ELECTRODE STRUCTURE FOR GENERATING IONS, AND ION GENERATING APPARATUS USING THE SAME

CROSS-REFERENCE TO RELATED APPLICATION

This application claims the benefit of Korean Patent Application No. 2004-58859, filed on Jul. 27, 2004 in the Korean Intellectual Property Office, the disclosure of which is incorporated herein by reference.

BACKGROUND OF THE INVENTION

1. Field of the Invention

The present invention relates to a ceramic electrode structure for generating ions, and an ion generating apparatus using the same and, more particularly, to a ceramic electrode structure for generating ions, designed to have an enhanced electrode structure, thereby enhancing performance of an ion generating apparatus, and an ion generating apparatus using the same.

2. Description of the Related Art

An ion generating apparatus is applied to air cleaners, air conditioners, humidifiers, etc.

Generally, when an alternate current is applied to the ion generating apparatus, the ion generating apparatus generates a positive ion and a negative ion, producing a hydroxide group (OH) or hydrogen peroxide ($H_2O_2$). Then, these elements are attached to bacteria, and result in oxidation of the bacteria or generation of ozone, thereby sterilizing the bacteria.

Japanese Patent Laid-open Publication No. 2003-36954 disclosed a ceramic electrode structure applied to a conventional ion generating apparatus. Although the apparatus of this document has an enhanced structure to effectively generate negative ions only, which are said to have positive health effects, a high frequency AC voltage is applied to a discharge electrode and an induction electrode of the apparatus, thereby generating a large amount of ozone. Furthermore, there is a need to further enhance the performance of ion generation.

SUMMARY OF THE INVENTION

The present invention has been made in view of the above and other problems, and an aspect of the present invention is to provide a ceramic electrode structure for generating ions, designed to have an enhanced electrode structure in order to further enhance performance of ion generation, and to restrict generation of ozone by applying a square pulse voltage to the ceramic electrode structure, and an ion generating apparatus using the ceramic electrode structure.

Additional aspects and/or advantages of the invention will be set forth in part in the description which follows and, in part, will be apparent from the description, or may be learned by practice of the invention.

In accordance with the present invention, these and/or other aspects are accomplished by providing a ceramic electrode structure for generating ions, comprising: a discharge electrode; an induction electrode, and a ceramic dielectric layer between the discharge electrode and the induction electrode, wherein the induction electrode has an area 2~3.5 times the area of the discharge electrode.

The ceramic electrode structure may further comprise a ceramic plate for securely mounting the induction electrode, and the discharge electrode may have an area 10~20% of the area of the ceramic plate.

The discharge electrode may comprise a pattern frame constituting an electrode line, an electrode portion to apply a voltage, and at least one discharge needle.

The discharge needle may have a length one or two times that of the thickness of the pattern frame, and may have a tip angle of 40~60°.

The pattern frame may have a thickness of 0.5~1 mm.

A horizontal distance between a distal end of the discharge needle and a distal end of the induction electrode may be 1.1~2.5 mm.

The pattern frame may have a geometrical shape in which polygons are adjacent to each other.

The electrode may have a capacitance of 20~40 pF.

A high voltage applied to the electrodes in a stable state is larger than an operating voltage initially applied to the electrodes.

The high voltage is 1.2~1.5 times larger than the operating voltage.

In accordance with another aspect, an ion generating apparatus comprises: an electrode structure having a plurality of electrodes to generate ions by means of a plasma discharge; and a square pulse generating part to apply a high square pulse voltage to the plurality of electrodes, wherein the plurality of electrodes comprise a discharge electrode and an induction electrode, and the induction electrode has an area 2~3.5 times that of the discharge electrode.

The square pulse voltage applied to the electrodes may be higher in a stable state than at an initial time.

BRIEF DESCRIPTION OF THE DRAWINGS

These and/or other aspects and advantages of the invention will become apparent and more readily appreciated from the following description of the exemplary embodiments, taken in conjunction with the accompanying drawings, of which:

FIG. 4 is a table showing dimensions of the ceramic electrode structures used in the experiments of FIGS. 3*a* to 3*e*, and the results thereof;

FIG. 9 shows an operation of sterilizing bacteria using the ion generating apparatus according to an embodiment of the present invention.

DETAILED DESCRIPTION OF THE ILLUSTRATIVE, NON-LIMITING EMBODIMENTS

Figure 1:
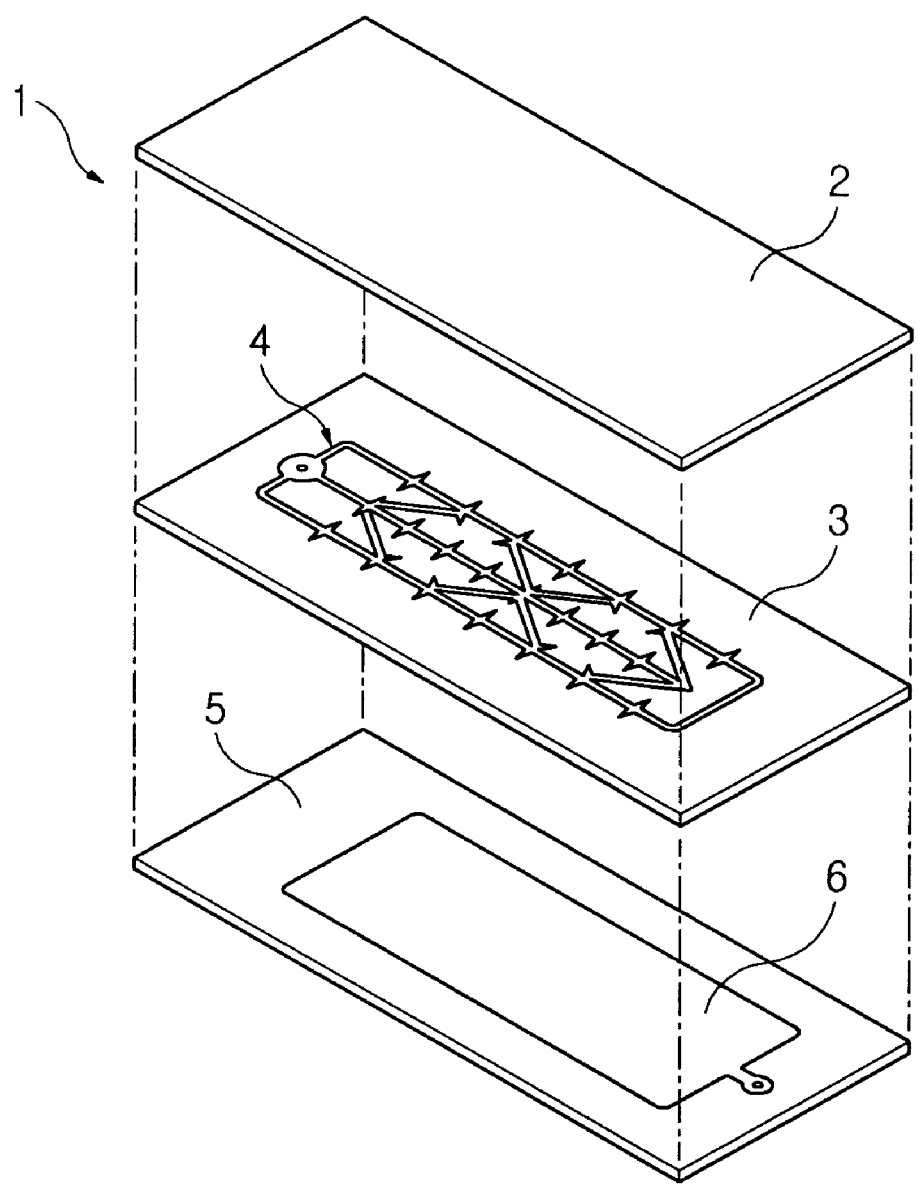
FIG. 1 is a perspective view of a ceramic electrode structure for generating ions according to an exemplary embodiment of the present invention.

Reference will now be made in detail to non-limiting exemplary embodiments of the present invention, examples of which are illustrated in the accompanying drawings, wherein like reference numerals refer to the like elements throughout the drawings. The exemplary embodiments are described below to explain the invention by referring to the figures, and are not intended to limit the scope of the invention in any way.

Referring to FIG. 1, an electrode structure 1 for generating ions according to an exemplary embodiment of the present invention comprises a ceramic coating layer 2, a discharge electrode 4, a ceramic dielectric layer 3, an induction electrode 6, and a ceramic plate 5, which are laminated in this order from the top down. The ceramic coating layer 2 covering the discharge electrode 4 protects the surface of the discharge electrode 4, and the ceramic insulation layer 3 is positioned between the discharge electrode 4 and the induction electrode 6, thereby insulating the discharge electrode 4 and the induction electrode 6 from each other.

Figure 2:
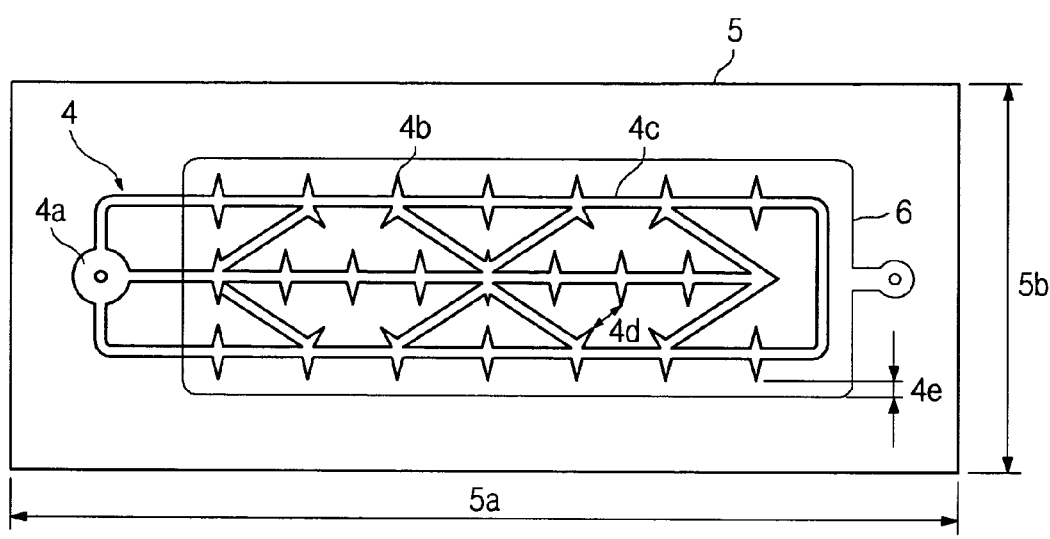
FIG. 2 is a plan view illustrating part of the ceramic electrode structure according to an exemplary embodiment of the present invention.

FIG. 2 is a plan view illustrating part of the ceramic electrode structure according to an exemplary embodiment of the present invention.

Referring to FIG. 2, the induction electrode 6 is securely mounted on the ceramic plate 5, and is mounted, at an upper portion thereof, with the discharge electrode 4 to correspond to the induction electrode 6. Since the discharge electrode 4 and the induction electrode 6 are printed with tungsten, which is an electric conductor, a high voltage applied to both ends of the electrodes causes a corona discharge, thereby generating ions. The discharge electrode 4 comprises a pattern frame 4c constituting an electrode line having a geometrical shape, an electrode portion 4a formed at one side of the pattern frame 4c, and a plurality of discharge needles 4b.

Various components related to the discharge electrode 4 determining an efficiency of ion generation will be set as follows. First, the discharge electrode 4 has an area 10~20% of an area $5a \times 5b$ of the ceramic plate 5. The pattern frame 4c has a thickness of 0.5~1.0 mm. Each of the discharge needles 4b has a length one or two times the thickness of the pattern frame, and has a tip angle of 40~60°. A horizontal distance 4e between the distal end of each of the outermost discharge needles 4b and the distal end of the induction electrode 6 is 1.1~2.5 mm. Furthermore, the pattern frame 4c has a geometrical shape in which polygons are arranged adjacent to each other, and is formed with the plurality of discharge needles 4b.

Figure 3A:
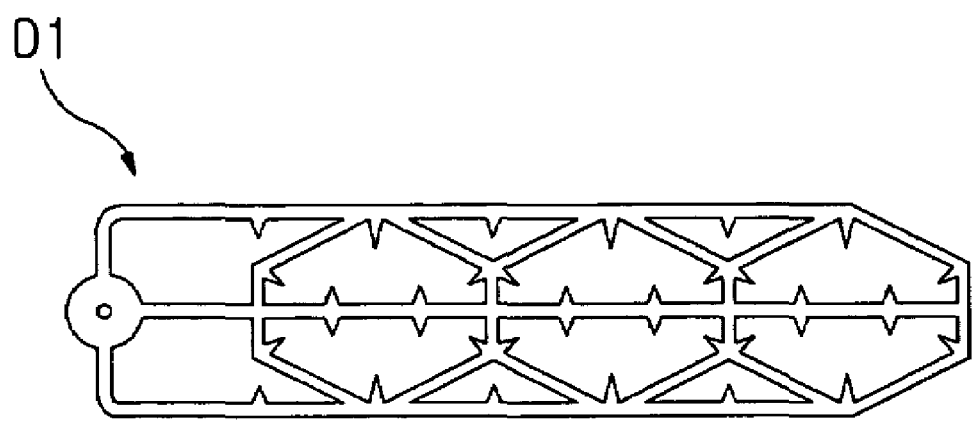
FIGS. 3*a* to 3*e* show models D1~D5 of discharge electrodes used in experiments.
Figure 3B:
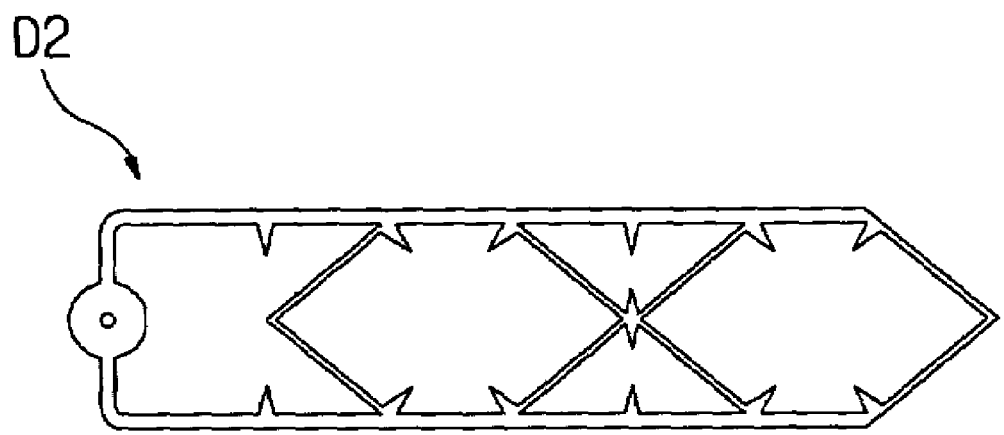
Figure 3C:
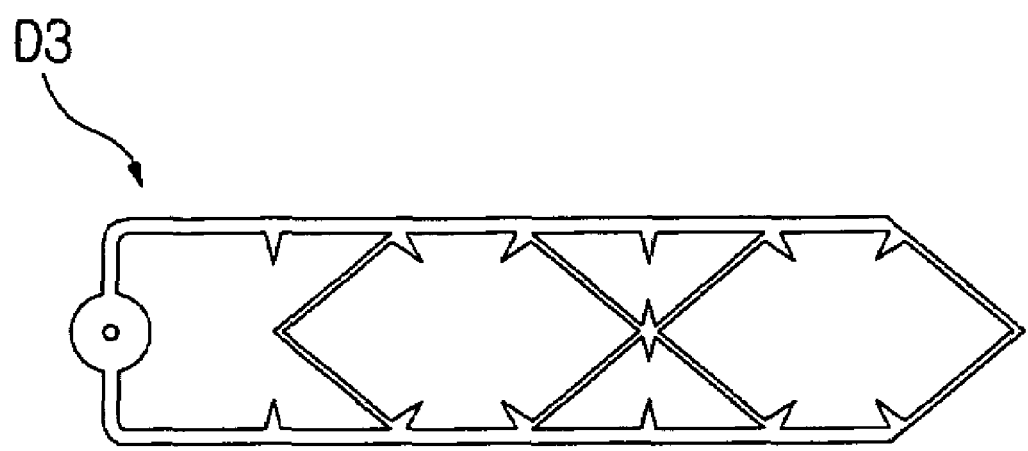
Figure 3D:
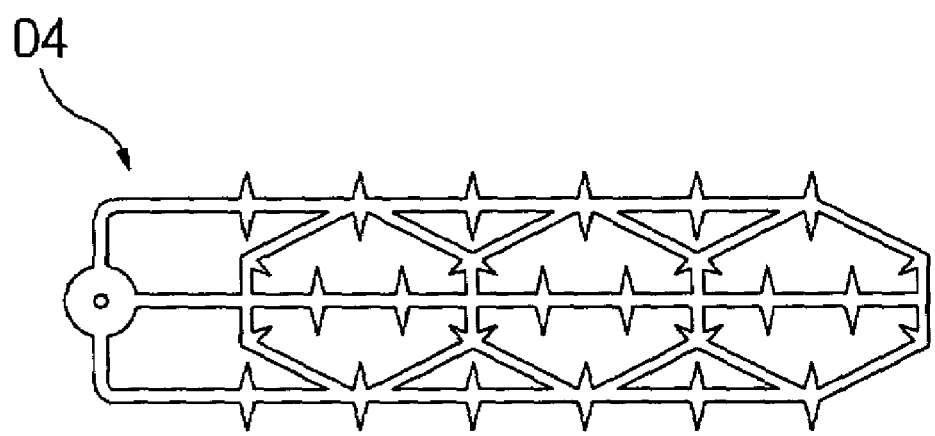
Figure 3E:
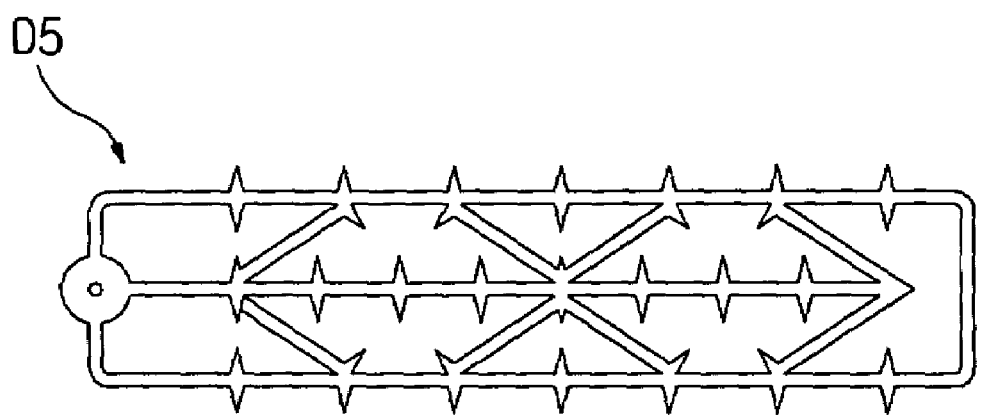
Figure 5:
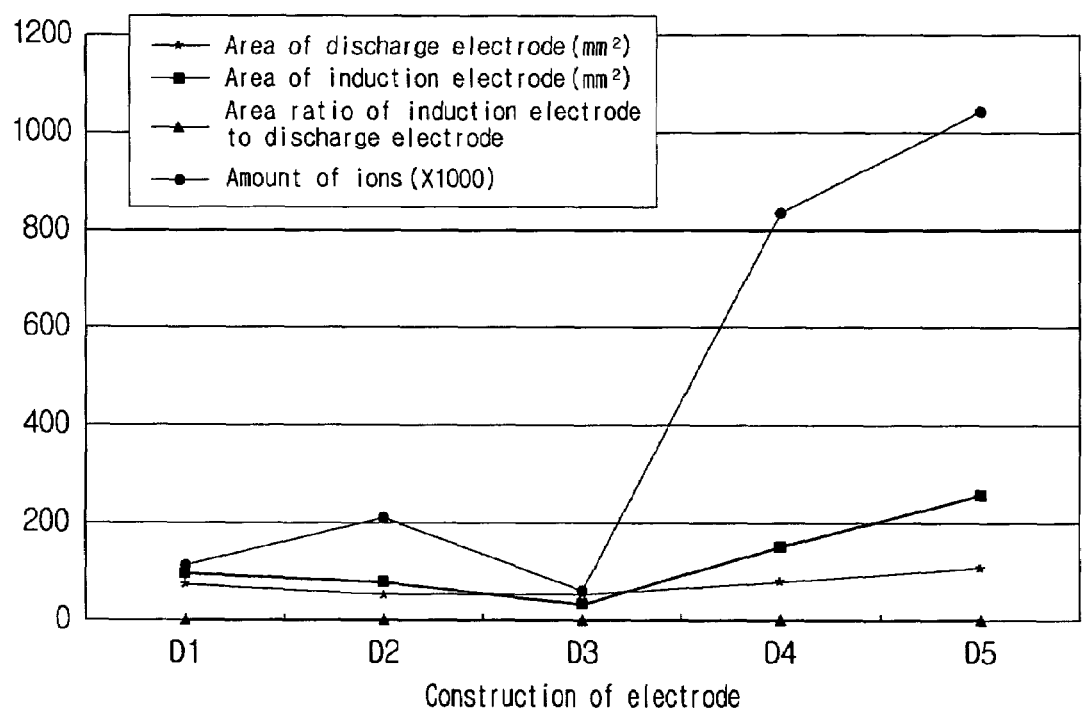
FIGS. 5 and 6 are graphical representations depicting the results of the experiment of FIG. 4.
Figure 6:
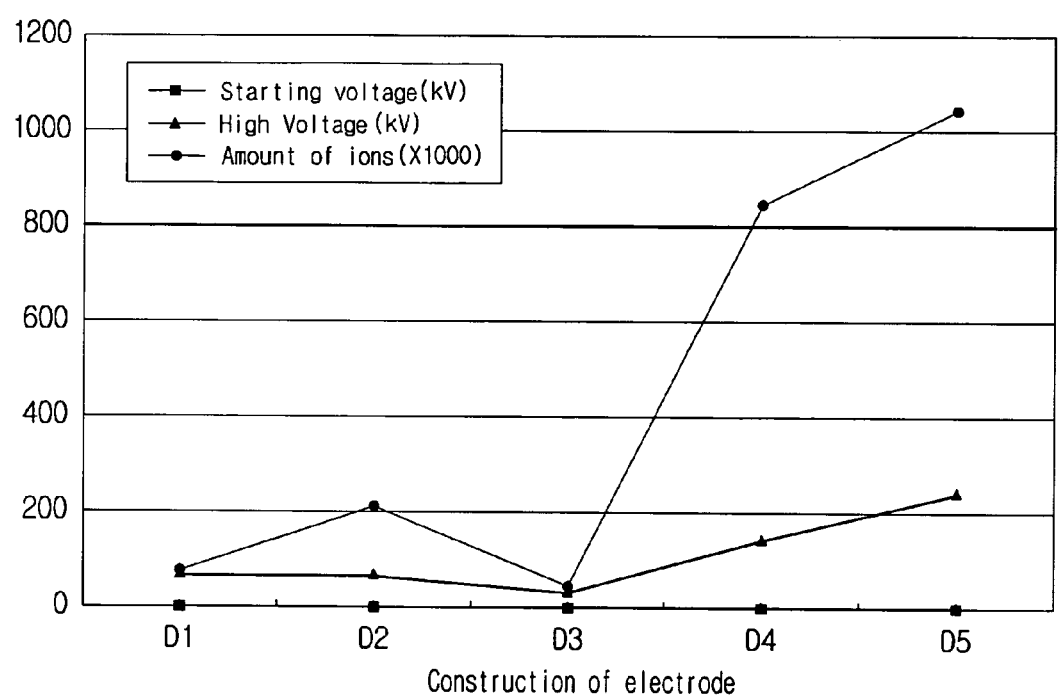

Meanwhile, in relation to a first model D1 shown in FIG. 3a, a second model D2 shown in FIG. 3b, a third model D3 shown in FIG. 3c, a fourth model D4 shown in FIG. 3d, and a fifth model D5 shown in FIG. 3e, experiments are carried out to explain the relationship between an area ratio of the induction electrode to the discharge electrode and an efficiency of ion generation, the relationship between a total area of the ceramic plate, the area ratio of the induction electrode to the discharge electrode, and the efficiency of ion generation, the relationship between an area of the discharge electrode 4, an area of the induction electrode 6, and the efficiency of ion generation, and the relationship between the operating voltage initially applied to the electrodes, the high voltage applied thereto in a stable state, and the efficiency of ion generation, etc., and results of the experiments are shown in FIGS. 4 to 6.

According to the results of the experiments, the fourth model D4 and the fifth model D5 exhibit a remarkably enhanced efficiency of ion generation. As conditions commonly applied to the fourth model D4 and the fifth model D5, the discharge electrode has an area of 40~80 mm$^2$, and the ratio of the area of the induction electrode to the discharge electrode is 2~3.5. The operating voltage initially applied to the electrodes is 2.4 kV or more, and the high voltage is 3.0 kV or more. A lower operating voltage is preferred, and the high voltage is 1.2~1.5 times that of the operating voltage.

Figure 7:
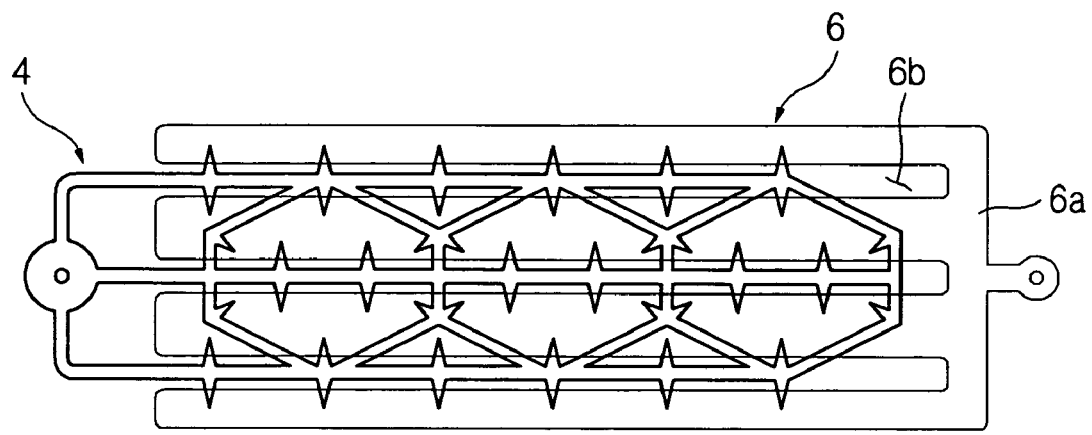
FIG. 7 shows another exemplary embodiment of an induction electrode consistent with the present invention.

As shown in FIG. 7, if a groove 6b is formed on a body 6a of a plate-shaped induction electrode 6, the induction electrode 6 can be used as a preferred ceramic electrode structure as long as the induction electrode 6 satisfies the above conditions.

Figure 8:
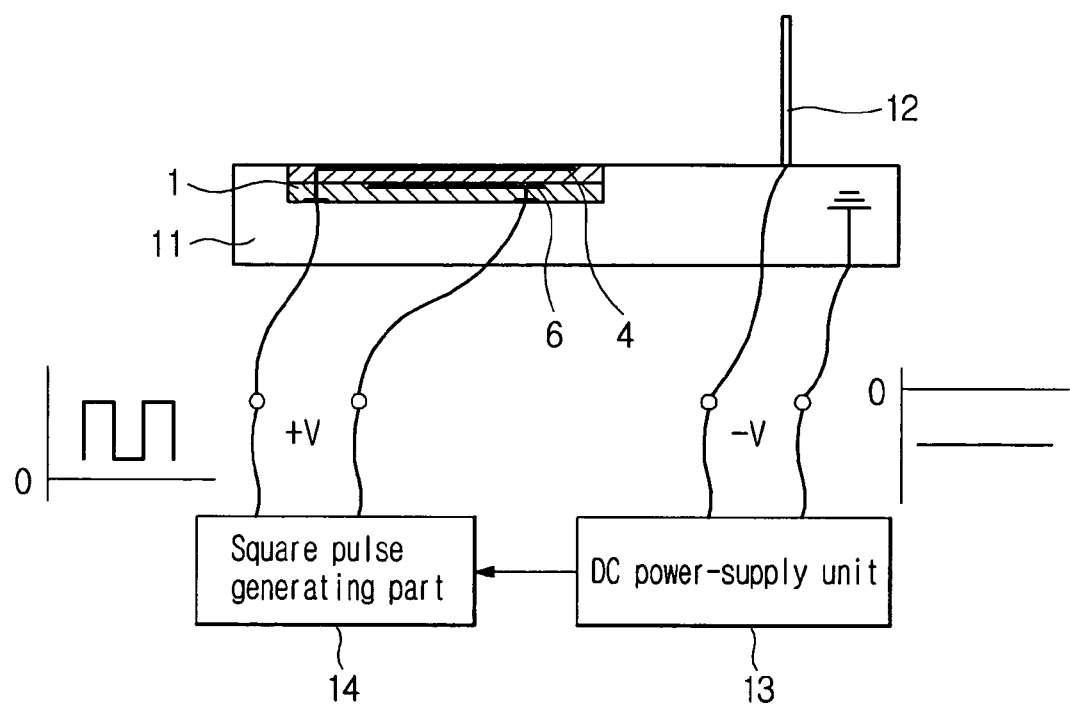
FIG. 8 shows an ion generating apparatus according to an embodiment of the present invention.

As shown in FIG. 8, the ceramic electrode structure 1 having the construction as described above can be applied to an ion generating apparatus.

The ion generating apparatus comprises a supporting plate 11, a ceramic electrode structure 1 at one side of the supporting plate 11, a needle-shaped electrode 12 at the other side of the supporting plate 11, a square pulse generating part 14 connected to electrical lead lines, which are connected to the discharge electrode 4 and the induction electrode 6 of the ceramic electrode structure 1, respectively, and a DC (Direct Current) power-supply unit 13 connected to the needle-shaped electrode 12 and another electrical lead line connected to the ground.

The DC power-supply unit 13 supplies a predetermined DC power (DC 12V) to the square pulse generating part 14. At this time, the square pulse generating part 14 converts the DC power to a square pulse voltage, and boosts the square pulse voltage. Then, the square pulse generating part 14 applies a boosted high square pulse voltage between the discharge electrode 4 and the induction electrode 6 through the lead lines. When the high square pulse voltage is applied to the ceramic electrode structure 1, ozone is restricted from being generated. Then, the DC power generating part 13 changes a polarity of the DC power to a negative polarity while boosting the DC power, and applies the boosted DC power of the negative polarity to the needle-shaped electrode 12.

In the case where the high square pulse voltage is applied to the ceramic electrode structure 1 and the DC power is applied to the needle-shaped electrode 12, as shown in FIG. 9, hydrogen ions H$^+$ are generated at the ceramic electrode structure 1, and electrons and superoxide anions O$_2^-$ are generated at the needle-shaped electrode 12. The hydrogen ions H$^+$ generated at the ceramic electrode structure 1 react with the electrons discharged from the needle-shaped electrode 12, and become hydrogen atom.

Thus, when the hydrogen atom and the superoxide anion O$_2^-$ are formed, a hydroperoxy radical (O—O—H) is formed. Electrons of the superoxide anion O$_2^-$ are offset by static electricity of bacteria. The O—O—H radical takes a hydrogen atom away from a protein indicative of a structural component of a cell membrane of the bacteria, such that it makes water. A protein molecule of the cell membrane from which the hydrogen atom is taken away is destroyed, and the cell membrane is also destroyed in such a way that sterilization is carried out.

As is apparent from the description, according to an embodiment of the present invention, the ceramic electrode structure has an enhanced shape, enhancing an efficiency of ion generation, thereby remarkably increasing the performance of ion generation, and a high square pulse voltage is applied to the ceramic electrode structure, thereby effectively restricting the generation of ozone.

While the invention has been particularly shown and described with reference to exemplary embodiments thereof, the invention is not limited to these embodiments. It would be appreciated by those skilled in the art that changes may be made in this embodiment without departing from the broad principles and spirit of the invention, the scope of which is defined in the claims and their equivalents.

What is claimed is:

1. A ceramic electrode structure for generating ions, comprising: a discharge electrode; an induction electrode, and a ceramic dielectric layer between the discharge electrode and the induction electrode,
   wherein the induction electrode has an area 2~3.5 times the area of the discharge electrode.

2. The ceramic electrode structure according to claim 1, wherein the ceramic electrode structure further comprises a ceramic plate for securely mounting the induction electrode, and the discharge electrode has an area 10~20% of the area of the ceramic plate.

3. The ceramic electrode structure according to claim 1, wherein the discharge electrode comprises a pattern frame constituting an electrode line, an electrode portion to apply a voltage, and at least one discharge needle.

4. The ceramic electrode structure according to claim 3, wherein the discharge needle has a length one or two times the thickness of the pattern frame, and has a tip angle of 40~60°.

5. The ceramic electrode structure according to claim 4, wherein the pattern frame has a thickness of 0.5~1 mm.

6. The ceramic electrode structure according to claim 3, wherein a horizontal distance between a distal end of the discharge needle and a distal end of the induction electrode is 1.1~2.5 mm.

7. The ceramic electrode structure according to claim 3, wherein the pattern frame has a geometrical shape in which polygons are adjacent to each other.

8. The ceramic electrode structure according to claim 1, wherein the electrode has a capacitance of 20~40 pF.

9. The ceramic electrode structure according to claim 1, wherein a high voltage applied to the electrodes in a stable state is larger than an operating voltage initially applied to the electrodes.

10. The ceramic electrode structure according to claim 1, wherein the high voltage is 1.2~1.5 times larger than the operating voltage.

11. An ion generating apparatus, comprising: an electrode structure having a plurality of electrodes to generate ions by means of plasma discharge; and a square pulse generating part to apply a high voltage having a square pulse to the plurality of electrodes,
    wherein the plurality of electrodes comprises a discharge electrode and an induction electrode, and the induction electrode has an area 2~3.5 times larger than that of the discharge electrode.

12. The ion generating apparatus according to claim 11, wherein the square pulse voltage applied to the electrodes is higher in a stable state than at an initial time.

* * * * *